United States Patent
Erkamp et al.

(10) Patent No.: US 11,944,487 B2
(45) Date of Patent: Apr. 2, 2024

(54) SIMULTANEOUS SENSOR TRACKING IN MEDICAL INTERVENTIONS

(71) Applicant: KONINKLIJKE PHILIPS N.V., Eindhoven (NL)

(72) Inventors: Ramon Erkamp, Swampscott, MA (US); Ameet Kumar Jain, Boston, MA (US); Alvin Chen, Cambridge, MA (US); Shyam Bharat, Arlington, MA (US); Kunal Vaidya, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 313 days.

(21) Appl. No.: 17/292,105

(22) PCT Filed: Nov. 11, 2019

(86) PCT No.: PCT/EP2019/080774
§ 371 (c)(1),
(2) Date: May 7, 2021

(87) PCT Pub. No.: WO2020/099281
PCT Pub. Date: May 22, 2020

(65) Prior Publication Data
US 2021/0393233 A1    Dec. 23, 2021

Related U.S. Application Data

(60) Provisional application No. 62/767,649, filed on Nov. 15, 2018.

(51) Int. Cl.
*A61B 34/20* (2016.01)
*A61B 8/08* (2006.01)
*A61B 90/00* (2016.01)

(52) U.S. Cl.
CPC .......... *A61B 8/0841* (2013.01); *A61B 34/20* (2016.02); *A61B 2034/2063* (2016.02); *A61B 2090/3786* (2016.02)

(58) Field of Classification Search
CPC .............. A61B 8/0841; A61B 34/20; A61B 2034/2063; A61B 2090/3786
See application file for complete search history.

(56) References Cited

U.S. PATENT DOCUMENTS

| 6,216,027 B1 * | 4/2001 | Willis ................. A61B 5/6855 600/462 |
| 2007/0049827 A1 * | 3/2007 | Donaldson ............ A61B 8/461 600/443 |

(Continued)

FOREIGN PATENT DOCUMENTS

| WO | 2018054969 A1 | 3/2018 |
| WO | 2018095793 A1 | 5/2018 |

OTHER PUBLICATIONS

International Search Report and Written Opinion of PCT/EP2019/080774, dated Feb. 26, 2020.

*Primary Examiner* — Serkan Akar
*Assistant Examiner* — Amal Aly Farag

(57) ABSTRACT

A controller (120) for simultaneously tracking multiple sensors in a medical intervention includes a circuit (121-181) that causes the controller (120) to execute a process. The process executed by the circuit (121-181) includes receiving first and second signals respectively from a first and a second passive ultrasound sensor (S2) used in the medical intervention. The first and second signals respectively include first and second sensor information indicative of respective locations of the first and the second passive ultrasound sensor (S2). The process executed by the circuit (121-181) also includes combining (120) the first signal and the second signal for transmission over only one channel, (Continued)

and providing the first signal and the second signal over the only one channel to a system (190) that determines the location of the first passive ultrasound sensor (S1) and the location of the second passive ultrasound sensor (S2) and that has only the one channel to receive the first signal and the second signal.

18 Claims, 11 Drawing Sheets

(56) References Cited

U.S. PATENT DOCUMENTS

| | | | |
|---|---|---|---|
| 2008/0146940 A1 | 6/2008 | Jenkins | |
| 2009/0175365 A1* | 7/2009 | Jun | H04L 5/0044 |
| | | | 375/295 |
| 2012/0215094 A1* | 8/2012 | Rahimian | A61B 6/481 |
| | | | 600/414 |
| 2013/0041252 A1 | 2/2013 | Vignon | |
| 2013/0058533 A1 | 3/2013 | Ren | |
| 2013/0289393 A1 | 10/2013 | Kruecker | |
| 2014/0243641 A1* | 8/2014 | Boveja | A61B 6/5247 |
| | | | 600/374 |
| 2015/0320492 A1* | 11/2015 | Ben-Haim | A61B 5/7278 |
| | | | 600/407 |
| 2016/0367322 A1* | 12/2016 | Jain | G01S 15/74 |
| 2017/0020562 A1 | 1/2017 | Erkamp | |
| 2017/0245941 A1 | 8/2017 | Bharat | |
| 2019/0307514 A1* | 10/2019 | Schwartz | A61B 5/063 |

* cited by examiner

SIMULTANEOUS SENSOR TRACKING IN MEDICAL INTERVENTIONS

CROSS-REFERENCE TO PRIOR APPLICATIONS

This application is the U.S. National Phase application under 35 U.S.C. § 371 of International Application No. PCT/EP2019/080774, filed on Nov. 11, 2019, which claims the benefit of U.S. Provisional Patent Application Ser. No. 62/767,649, filed Nov. 15, 2018. These applications are hereby incorporated by reference herein.

BACKGROUND OF THE INVENTION

An interventional medical device such as a needle can be tracked using an ultrasound probe that transmits ultrasound beams to the interventional medical device. Localization of the interventional medical device in an ultrasound image may be hampered if the interventional medical device lacks echogenic properties and is therefore poorly visible in the ultrasound image. To resolve this issue, a piezoelectric sensor can be applied on or in the interventional medical device, often close to the device tip insofar as a user is typically interested in the location of the device tip. The piezoelectric sensor is a passive ultrasound sensor (e.g., PZT, PVDF, copolymer or other piezoelectric material) and is placed on or in the interventional medical devices. The passive ultrasound sensor passively listens to and measures the incident ultrasound waves of the ultrasound beams without responding as the ultrasound beams sweep the field of view of a diagnostic B-mode ultrasound imaging field. Analysis of the resultant measurements yields an estimate of the position of the passive ultrasound sensor on the interventional medical device in the frame of reference of the field of view of the diagnostic B-mode ultrasound image. Specifically, time-of-flight measurements provide the axial/radial distance of the passive ultrasound sensor from the imaging array, while amplitude measurements and knowledge of the beam firing sequence provide the lateral/angular position of the passive ultrasound sensor. The position of the device tip can then be overlaid on the ultrasound image for enhanced visualization of the interventional medical device, and the positions and their histories can be logged for tracking and other applications. An interventional medical device is typically tracked using a single ultrasound probe.

In a known system, an ultrasound probe emits an imaging beam that sweeps across a passive ultrasound sensor on a tool tip of an interventional medical device such as a needle. An image of tissue is fed back by the ultrasound probe. A location of the passive ultrasound sensor on the tool tip of the interventional medical device is provided as a tip location upon determination by a signal processing algorithm. The tip location is overlaid on the image of tissue as an overlay image. The image of tissue, the tip location, and the overlay image are all displayed on a display.

As applications for device tracking technology are developed, at least initially commercial versions of device tracking systems are or will likely be single channel systems that only allow tracking of a single sensor, such as by having only a single input interface with a single channel designed to accommodate signals from a single sensor.

SUMMARY OF THE INVENTION

According to an aspect of the present disclosure, a controller for simultaneously tracking multiple sensors in a medical intervention includes a circuit that causes the controller to execute a process. The process executed by controller includes receiving, from a first passive ultrasound sensor used in the medical intervention, a first signal with first sensor information indicative of a location of the first passive ultrasound sensor, and receiving, from a second passive ultrasound sensor used in the medical intervention, a second signal with second sensor information indicative of a location of the second passive ultrasound sensor. The process executed by the controller also includes combining the first signal and the second signal for transmission over one and only one channel; and providing the first signal and the second signal over the one and only one channel to a system that determines the location of the first passive ultrasound sensor and the location of the second passive ultrasound sensor and that has only the one and only one channel to receive the first signal and the second signal.

According to another aspect of the present disclosure, a method for simultaneously tracking multiple sensors in a medical intervention includes receiving, from a first passive ultrasound sensor used in the medical intervention, a first signal with first sensor information indicative of a location of the first passive ultrasound sensor, and receiving, from a second passive ultrasound sensor used in the medical intervention, a second signal with second sensor information indicative of a location of the second passive ultrasound sensor. The method also includes combining the first signal and the second signal for transmission over one and only one channel, and providing the first signal and the second signal over the one and only one channel to a system that determines the location of the first passive ultrasound sensor and the location of the second passive ultrasound sensor and that has only the one and only one channel to receive the first signal and the second signal.

According to yet another aspect of the present disclosure, a system for simultaneously tracking multiple sensors in a medical intervention includes a first passive ultrasound sensor; a second passive ultrasound sensor; and a controller that includes a circuit that causes the controller to execute a process. The process executed by the controller includes receiving, from the first passive ultrasound sensor used in the medical intervention, a first signal with first sensor information indicative of a location of the first passive ultrasound sensor, and receiving, from the second passive ultrasound sensor used in the medical intervention, a second signal with second sensor information indicative of a location of the second passive ultrasound sensor. The process executed by the controller also includes combining the first signal and the second signal for transmission over one and only one channel, and providing the first signal and the second signal over the one and only one channel to a system that determines the location of the first passive ultrasound sensor and the location of the second passive ultrasound sensor and that has only the one and only one channel to receive the first signal and the second signal.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION OF THE EMBODIMENTS

Figure 1A:
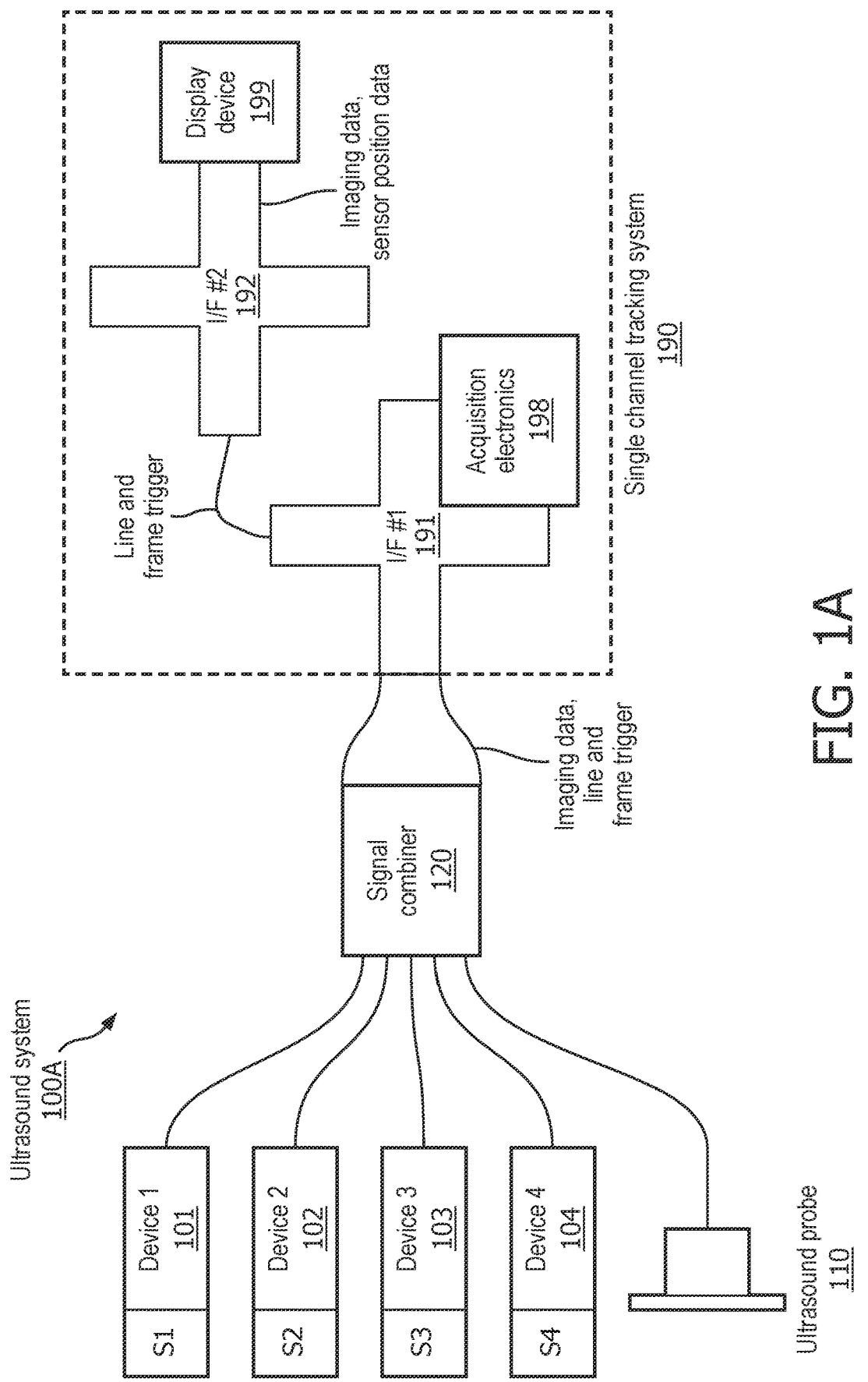
FIG. 1A illustrates a system for simultaneous sensor tracking in medical interventions, in accordance with a representative embodiment.

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only, and is not intended to be limiting. As used in the specification and appended claims, the singular forms of terms 'a', 'an' and 'the' are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In view of the foregoing, the present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

As described herein, simultaneous sensor tracking in medical interventions allows tracking of multiple devices on a tracking system that has only one channel (e.g., of A/D conversion) for an incoming sensor signal. This will allow initial development of single input channel tracking systems that can be enabled later to adapt to tracking of multiple devices, even while the single channel tracking systems retain one and only one channel to receive a signal from a passive ultrasound sensor. Later adaptation can be achieved by retrofitting the initial single input channel tracking systems to allow multiple device tracking. Accordingly, simultaneous sensor tracking medical interventions enhances device tracking and navigation device visualization for image guided therapy.

FIG. 1A illustrates a system for simultaneous sensor tracking in medical interventions, in accordance with a representative embodiment.

In FIG. 1A, an ultrasound system 100A has a first interventional medical device 101 that includes a first passive ultrasound sensor S1, a second interventional medical device 102 that includes a second passive ultrasound sensor S2, a third interventional medical device 103 that includes a third passive ultrasound sensor S3, and a fourth interventional medical device 104 that includes a fourth passive ultrasound sensor S4. Any of the interventional medical devices in the ultrasound system 100A of FIG. 1A may include more than one passive ultrasound sensor. Additionally, medical interventions may include use of any number, including only one, of the first interventional medical device 101, the second interventional medical device 102, the third interventional medical device 103, and the fourth interventional medical device 104. For example, most embodiments described herein include only the first interventional medical device 101 and the second interventional medical device 102. The focus of the teachings herein is more on the passive ultrasound sensors such as the first passive ultrasound sensor S1 and the second passive ultrasound sensor S2 than on any particular interventional medical device.

In FIG. 1A, an ultrasound probe 110 emits ultrasound beams that are detected by any of the passive ultrasound sensors on the interventional medical devices. Each of the passive ultrasound sensors sends sensor data over a wired or wireless connection to the signal combiner 120. The sensor data is generated by the passive ultrasound sensors based on the detected ultrasound beams from the ultrasound probe 110.

In FIG. 1A, the signal combiner 120 combines the signals from the passive ultrasound sensors to combined sensor data to obtain combined sensor data. The signal combiner 120 also receives the imaging data and a line and frame trigger from the ultrasound probe 110. The signal combiner 120 in FIG. 1A is representative of a controller that implements the features described herein, and may include a variety of circuits in accordance with different embodiments. Thus, the signal combiner 120 may be a controller, or may be an element of a controller as the term is used herein.

A single channel tracking system includes a first interface 191 that interfaces with acquisition electronics 198, and a second interface 192 that interfaces with a display device 199. The single channel tracking system 190 may also include or interface with acquisition electronics 198 and/or a display device 199. The signal combiner 120 sends combined sensor data from the passive ultrasound sensors to the first interface 191. The signal combiner 120 also sends the imaging data and the line and frame trigger from the ultrasound probe 110 to the first interface 191.

In FIG. 1A and other FIGS. herein, a single channel is the channel between the signal combiner 120 and the single channel tracking system 190. The single channel may reference a single port, a single input, or aspects of the single channel tracking system 190 that limit the single channel tracking system 190 to processing signals of only one passive ultrasound sensor but for the teachings of the present disclosure. Thus, the single channel may be a channel from the signal combiner 120 (or circuits described in detail for later embodiments) to the single channel tracking system 190 such as to the first interface 191.

The first interface 191 interfaces with acquisition electronics 198 to acquire sensor position data based on the combined sensor data. The first interface 191 sends the imaging data and the line and frame trigger from the ultrasound probe 110 to the second interface 192. The first interface 191 also sends the acquired sensor position data from the acquisition electronics 198 to the second interface 192. The second interface 192 interfaces with the display device 199. The display device 199 displays ultrasound images based on the imaging data, and sensor positions superimposed on the imaging data based on the acquired sensor position data. The ultrasound images and the sensor positions are synchronized based on the line and frame trigger from the ultrasound probe.

The signal combiner 120 is shown as a generic block in FIG. 1A but is representative of a circuit that includes circuit elements as shown in individual embodiments below. The signal combiner 120 provides at least a first signal from a first passive ultrasound sensor S1 and a second signal from a second passive ultrasound sensor over one and only one channel to the single channel tracking system 190. The single channel tracking system 190 determines the location of the first passive ultrasound sensor S1 and the second passive ultrasound sensor S2 based on the first signal and the second signal. The single channel tracking system 190 also has one and only one channel to receive the first signal and the second signal, or alternatively uses one and only one channel to receive the first signal and the second signal even if more than one channel is available.

Figure 1B:
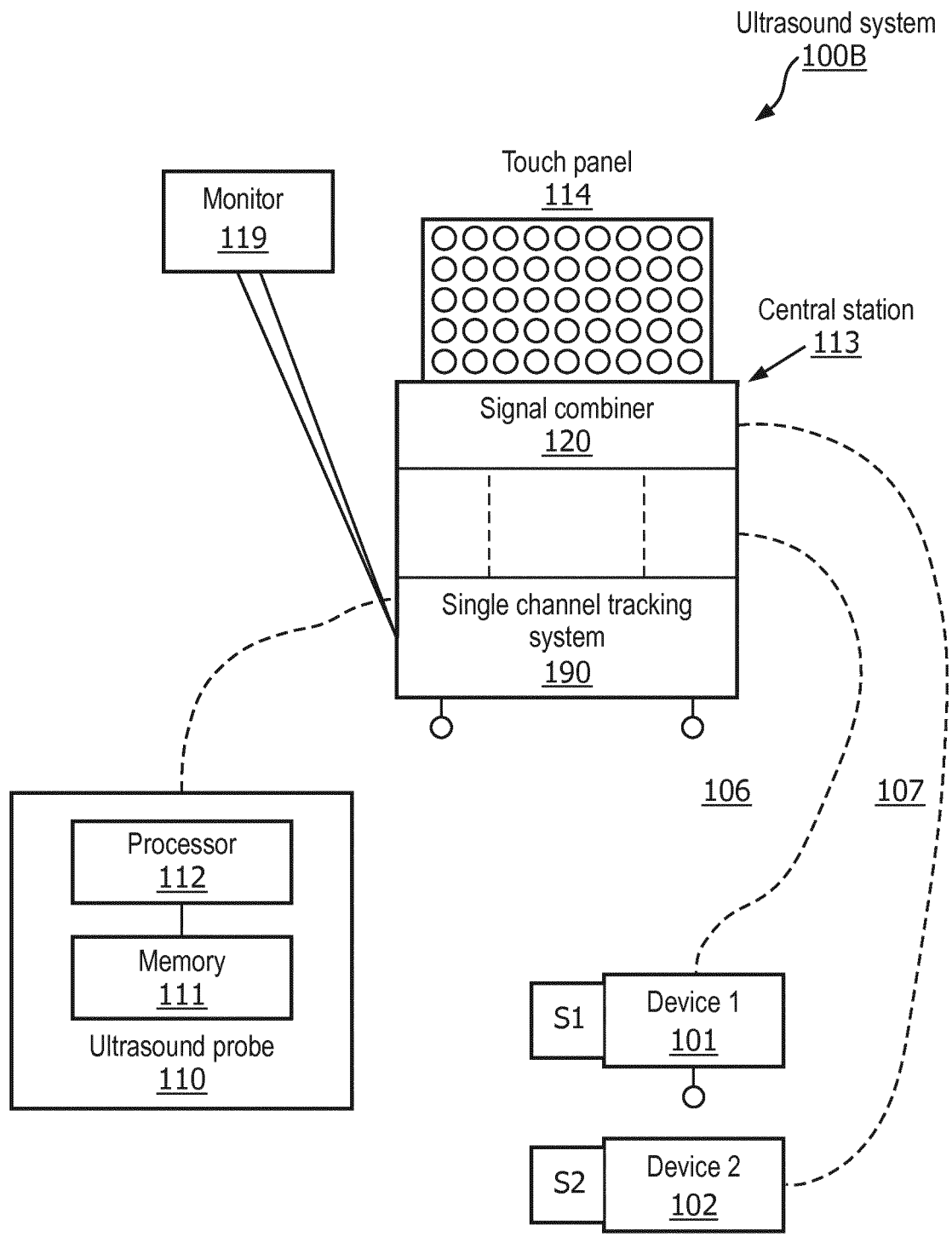
FIG. 1B illustrates another system for simultaneous sensor tracking in medical interventions, in accordance with a representative embodiment.

In FIG. 1B, a single signal can be created by uniquely encoding signals from each of multiple interventional medical devices with passive ultrasound sensors installed therein or thereon. The combined signal can later be decoded by the single channel tracking system, optionally exploiting a communication protocol. The physical implementation of the signal combiner 120 may be a box such as an add-on module shipped to a customer, wherein one end of the box connects to the interventional medical devices and the ultrasound probe 110, and the other end connects to the single channel tracking system 190.

FIG. 1B illustrates another system for simultaneous sensor tracking in medical interventions, in accordance with a representative embodiment.

In FIG. 1B, an ultrasound system 100B includes a central station 113 with the single channel tracking system 190 provided therein. The central station 1130 may include a controller that includes the signal combiner 120 as in FIG. 1A. The signal combiner 120 may be a module attached to, integrated with, or otherwise implemented in, on or with the central station 113 in FIG. 1B. That is, the signal combiner 120 may be provided by a manufacturer separately from the central station 113 or may be an add-on module of circuitry that interfaces with the one and only one channel of the single channel tracking system 190. The signal combiner 120 may be or include a controller that includes a circuit that causes the controller to execute processes as described herein.

The central station 113 also includes a touch panel 114, a monitor 119. The ultrasound system 199b also includes the first interventional medical device 101 connected to the central station 113 by a data connection 106 (e.g., a wired or wireless data connection), and a second interventional medical device 102 connected to the central station 113 by a data connection 107. The ultrasound probe 110 includes a memory 111 that stores instructions and a processor 112 that executes the instructions. In the context of FIG. 1B, a controller is implemented by, in or on the signal combiner 120 insofar as the signal combiner 120 interfaces with the first interventional medical device 101, the second interventional medical device 102, and the single channel tracking system 190, and more indirectly with the ultrasound probe 110 and the monitor 119 via the single channel tracking system 190.

A controller as described for FIG. 1B and other embodiments herein may be implemented in a variety of forms, either by modifying an existing system or type of system, or by providing a new system or type of system such as a stand-alone module.

The first interventional medical device 101 may be provided at the end of a wire or similar instrument. The first interventional medical device 101 is inserted into a patient during a medical intervention managed by a human interventionalist. The first interventional medical device 101 may be, for example, an intravascular ultrasound probe that produces ultrasound imagery, though sensor signals from a passive ultrasound sensor S1 on the first interventional medical device 101 are the signals of interest relative to the first interventional medical device 101 for the purposes of this description. The second interventional medical device 102 may also be provided at the end of a wire or similar instrument. The second interventional medical device 102 is inserted into a patient during a medical intervention managed by a human interventionalist. The second interventional medical device 102 may be, for example, a needle with the second passive ultrasound sensor S2 disposed on a tip to provide signals of interest relative to the second interventional medical device 102 for the purposes of this description.

More particularly, in the embodiment of FIG. 1B, the passive ultrasound sensor signals from the first passive ultrasound sensor S1 are synchronized with ultrasound imagery from the ultrasound probe 110. Time-of-flight measurements provide the axial/radial distance of the first passive ultrasound sensor S1 from the ultrasound probe 110. Amplitude measurements and knowledge of the beam firing sequence may provide the lateral position of the first passive ultrasound sensor S1. Since phase can correspond to time-of-flight, phase may be used instead of time-of-flight insofar as phase may provide higher measurement precision. Additionally, in the embodiment of FIG. 1B, the passive ultrasound sensor signals from the second passive ultrasound sensor S2 are synchronized with ultrasound imagery from the ultrasound probe 110. Time-of-flight measurements provide the axial/radial distance of the second passive ultrasound sensor S2 from the ultrasound probe 110. Amplitude measurements and knowledge of the beam firing sequence may provide the lateral position of the second passive ultrasound sensor S2. Again, since phase can correspond to time-of-flight, phase may be used instead of time-of-flight insofar as phase may provide higher measurement precision.

The monitor 119 may display two-dimensional positions of the first passive ultrasound sensor S1 and two-dimensional positions of the second passive ultrasound sensor S2. The monitor 119 may also display the ultrasound images based on ultrasound imagery from the ultrasound probe 110. That is, the monitor 119 also displays the conventional imagery otherwise obtained using ultrasound probes such as ultrasound probe 110, including ultrasound imagery of regions of interest of human anatomy and/or of the first interventional medical device 101 and the second interventional medical device 102.

The first passive ultrasound sensor S1 and the second passive ultrasound sensor S2 may each or both include one or multiple piezoelectric elements (e.g., PZT). When multiple piezoelectric elements are included, measurements from the multiple piezoelectric elements can be averaged to provide an overall position of the corresponding interventional medical device. Additionally, since relative positional arrangements of multiple piezoelectric elements may be known, an overall relative pose, 3-dimensional directionality, or even a predicted trajectory of the corresponding interventional medical device can also be determined from the relative measurements.

By way of explanation, the first interventional medical device 101 and the second interventional medical device 102 are placed internally into a patient during a medical procedure. Locations of the first interventional medical device 101 and the second interventional medical device 102 can be seen on imagery generated from the ultrasound image signals from the ultrasound probe 110.

Figure 2:
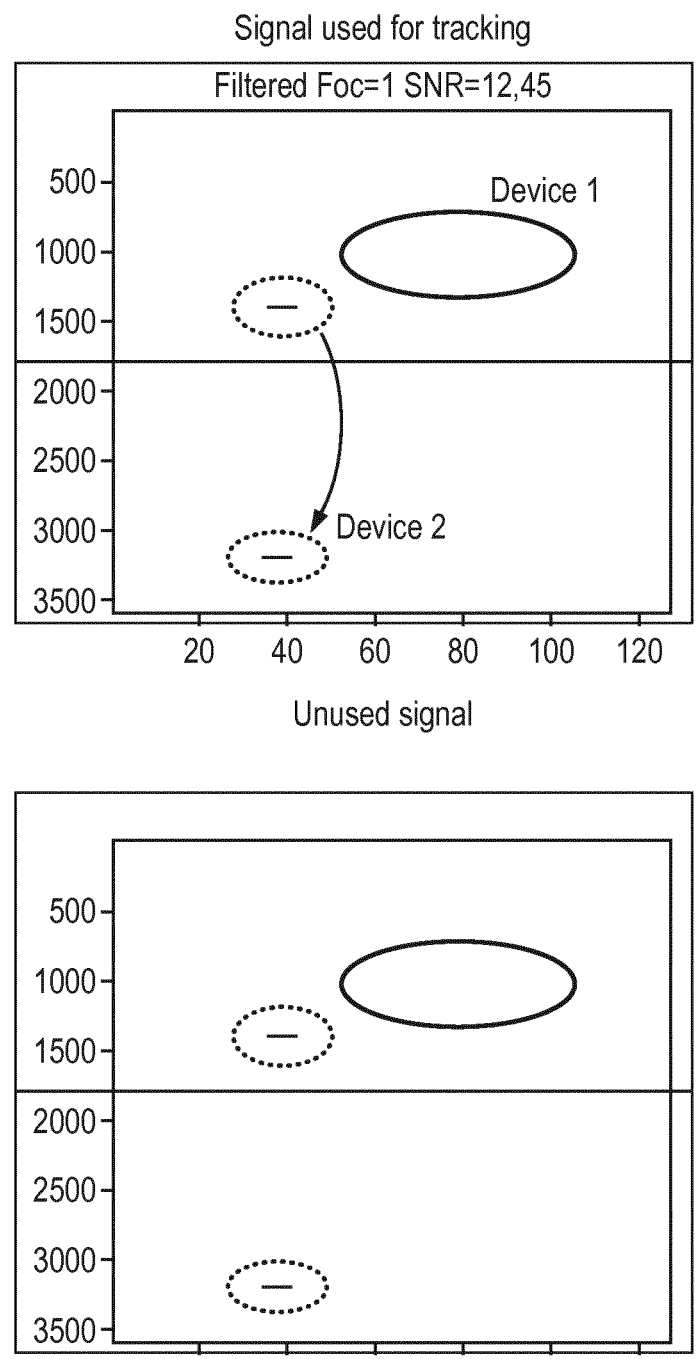
FIG. 2 illustrates timing for simultaneous sensor tracking in medical interventions in accordance with an embodiment.

FIG. 2 illustrates timing for simultaneous sensor tracking in medical interventions in accordance with an embodiment.

Passive ultrasound sensors such as the first passive ultrasound sensor S1 and the second passive ultrasound sensor S2 use one way acoustic beam travel, in that the acoustic beams from the ultrasound probe 110 are received but the sensor data from the first passive ultrasound sensor S1 and the second passive ultrasound sensor S2 are provided over a wire or wireless data connection. That is, two-way acoustic beam travel involves reflections to generate ultrasound imagery at the ultrasound probe 110, and the one-way acoustic beam travel for sensor tracking does not use the reflections for the sensor tracking. Accordingly, in the time window from one ultrasound beam firing from the ultrasound probe 110 to the next beam firing from the ultrasound probe 110, only the first half of the time contains relevant tracking information, and the other half of the time will not have an acoustic signal.

In the case of two passive ultrasound devices being tracked, the sensor signal from the second passive ultrasound sensor S2 can be delayed such that it will fall in the unused signal area. This is illustrated in FIG. 2. Without a delay line, the signal from the second passive ultrasound sensor S2 would show up at the smaller oval shown by the broken line in the upper half where it could interfere with the signal from the first passive ultrasound sensor S1. However, adding the delay line moves the signal from the second passive ultrasound sensor S2 down to the smaller oval shown by the broken line in the lower half. Now the two signals will not interfere, and there is no ambiguity regarding what peak belongs to the first passive ultrasound sensor S1 and what peak belongs to the second passive ultrasound sensor S2.

Figure 3:
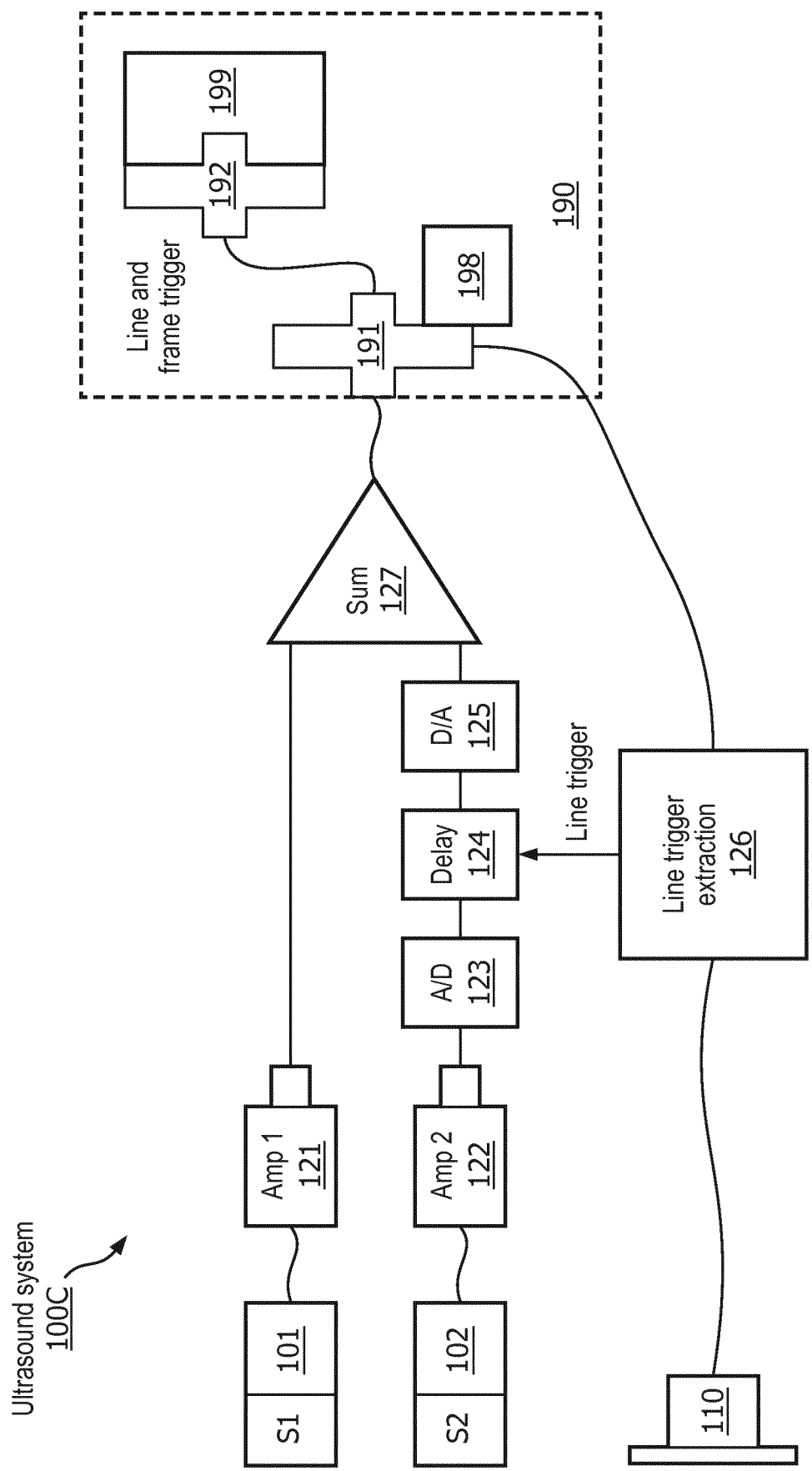
FIG. 3 illustrates another system for simultaneous sensor tracking in medical interventions, in accordance with the representative embodiment of FIG. 2.

FIG. 3 illustrates another system for simultaneous sensor tracking in medical interventions, in accordance with the representative embodiment of FIG. 2.

In FIG. 3, an ultrasound system 100C includes a first interventional medical device 101 with a first passive ultrasound sensor S1 disposed therein or thereon, and a second interventional medical device 102 with a second passive ultrasound sensor S2 disposed therein or thereon. The first passive ultrasound sensor S1 is connected via a data connection to a first amplifier 121, and the second passive ultrasound sensor S2 is connected via a different data connection to a second amplifier 122. The output of the second amplifier 122 is provided to an analog-to-digital converter 123, which in turn provides a digital output to the delay element 124, which in turn provides an output to a digital-to-analog converter 125. The output of the first amplifier 121 and the digital-to-analog converter 125 are provided to a summer 127.

The first amplifier 121 amplifies the sensor signal from the first passive ultrasound sensor S1. The second amplifier 122 amplifiers the sensor signal from the second passive ultrasound sensor S2. The analog-to-digital converter 123 digitizes the amplified analog signal from the second amplifier 122. The delay element 124 adds a delay to the digitized amplified signal from the analog-to-digital converter 123. The digital-to-analog converter 125 converts the delayed digitized amplified signal back to an analog signal. The analog signals from the first amplifier 121 and the digital-to-analog converter 125 are provided to the summer 127, which combines the analog signals as the first signal from the first passive ultrasound sensor S1 and the second signal from the second passive ultrasound sensor S2 and provides the combined signal over one and only one channel to the first interface 191 of the single channel tracking system 190.

Additionally, a line trigger extraction circuit 126 in FIG. 3 extracts a line trigger from the signals provided from the ultrasound probe 110. The line trigger is provided to the delay element 124 to ensure that the sensor data from the second passive ultrasound sensor S2 is properly delayed so as not to interfere with the sensor data from the first passive ultrasound sensor S1.

In the embodiment of FIG. 3, the delay line for the second passive ultrasound sensor S2 has a programmable duration and may be set to half of the beam-to-beam time frame or something close such as within 45% to 55% of the beam-to-beam time frame. In FIG. 3, the delay is implemented by converting the signal from the second passive ultrasound sensor S2 to digital, storing the converted signal in a buffer memory such as a circular buffer used as the delay element 124, digitally reading out the delayed converted signal from the buffer memory, and converting the delayed converted signal back to an analog output.

As explained above, the process includes the delay element 124 inserting a delay to the digitized amplified signal from the analog-to-digital converter 123. The delay is inserted to one (and only one) of the first signal from the first amplifier 121 and the second signal from the second amplifier 122 (i.e., to the second signal from the second amplifier 122 in FIG. 3). The delay can be removed by the single channel tracking system 190 insofar as the single channel tracking system 190 is able to determine location of the first passive ultrasound sensor S1 and the second passive ultrasound sensor S2 based on the first signal from the first amplifier 121 and the delayed second signal from the second amplifier 122.

Figure 4:
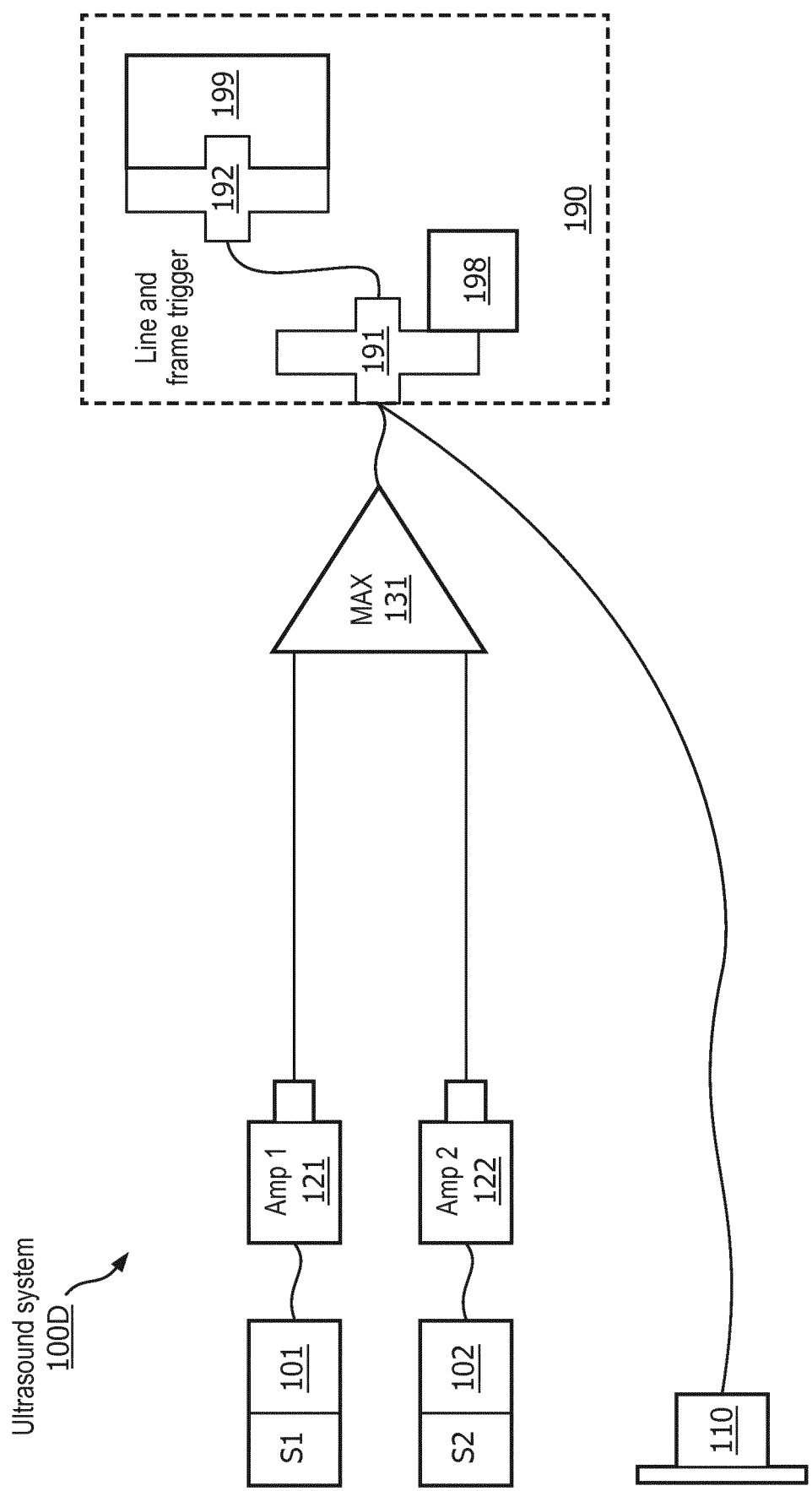
FIG. 4 illustrates another system for simultaneous sensor tracking in medical interventions, in accordance with another representative embodiment.

FIG. 4 illustrates another system for simultaneous sensor tracking in medical interventions, in accordance with another representative embodiment.

In FIG. 4, an ultrasound system 100D includes the first interventional medical device 101 with the first passive ultrasound sensor S1 disposed therein or thereon and the second interventional medical device 102 with the second passive ultrasound sensor S2 disposed therein or thereon. The first passive ultrasound sensor S1 is connected via the data connection to the first amplifier 121, and the second passive ultrasound sensor S2 is connected via the different data connection to a second amplifier 122. The output of the first amplifier 121 and the output of the second amplifier 122 are provided to a maximum circuit 131 that identifies the peak magnitudes of each (i.e., both) of the first signal from the first passive ultrasound sensor S1 and the second signal from the second passive ultrasound sensor S2.

That is, the maximum circuit 131 performs functions including isolating a largest peak of the first signal and a largest peak of the second signal and filtering signal components with peaks smaller than the largest peak of the first signal and the largest peak of the second signal. As a result, the maximum circuit 131 provides only signal components with the largest peak of the first signal and the largest peak of the second signal to the single channel tracking system 190. The single channel tracking system 190 can then determine the location of the first passive ultrasound sensor S1 and the location of the second passive ultrasound sensor S2.

The maximum circuit 131 includes at least an analog filter to filter signal components smaller than the largest peak of the first signal and the largest peak of the second signal. The maximum circuit 131 may also include analog-to-digital converters and digital-to-analog converters, and a logical element such as a processor (e.g., a microprocessor or an application-specific integrated circuit or ASIC). The logical element may be used to logically isolate the largest peak of the first signal and the largest peak of the second signal from signal components with smaller peaks.

By way of explanation, in the embodiment of FIGS. 2 and 3, multiple passive ultrasound sensors including the first passive ultrasound sensor S1 and the second passive ultrasound sensor S2 each emit sensor signals. All of the sensor signals are added in the summer 127. If the peaks are sufficiently separated, the individual device peaks can be detected. However, if side lobes in the sensor signals are significant and the signal separation is small, overlapping side lobes can occur and may add up to be larger than the peaks of the first signal and the second signal from the individual sensors, giving rise to false peaks. In the embodiment of FIG. 4, only the largest peak of the first signal and the largest peak of the second signal are transmitted to downstream hardware. If the peak magnitudes of the first signal and the second signal are comparable, good peak separation can be provided even when the peaks are in close proximity.

Moreover, even if the first passive ultrasound sensor S1 and the second passive ultrasound sensor S2 have different sensor geometries and therefore different sensitivity, amplifiers can be used so as to adjust amplifier gains for the first passive ultrasound sensor S1 or the second passive ultrasound sensor S2 to achieve similar peak signals. The adjustments may be performed automatically, such as by monitoring the peak signal over one or more imaging frames with an analog filter, and then the maximum circuit 131 (or another element) gradually adjusting amplifier gains for one of the first signal and the second signal to reach a desired peak signal. Such adjusting of the amplifier gains may also reduce demand on the dynamic range for the downstream hardware and allows for a wider range of sensor sensitivities. Accordingly, amplifier gains of one and only one of the first signal and the second signal can be adjusted so that the first signal or the second signal with adjusted amplifier gains has a largest peak closer in magnitude to the largest peak of the other of the first signal and the second signal.

Figure 5:
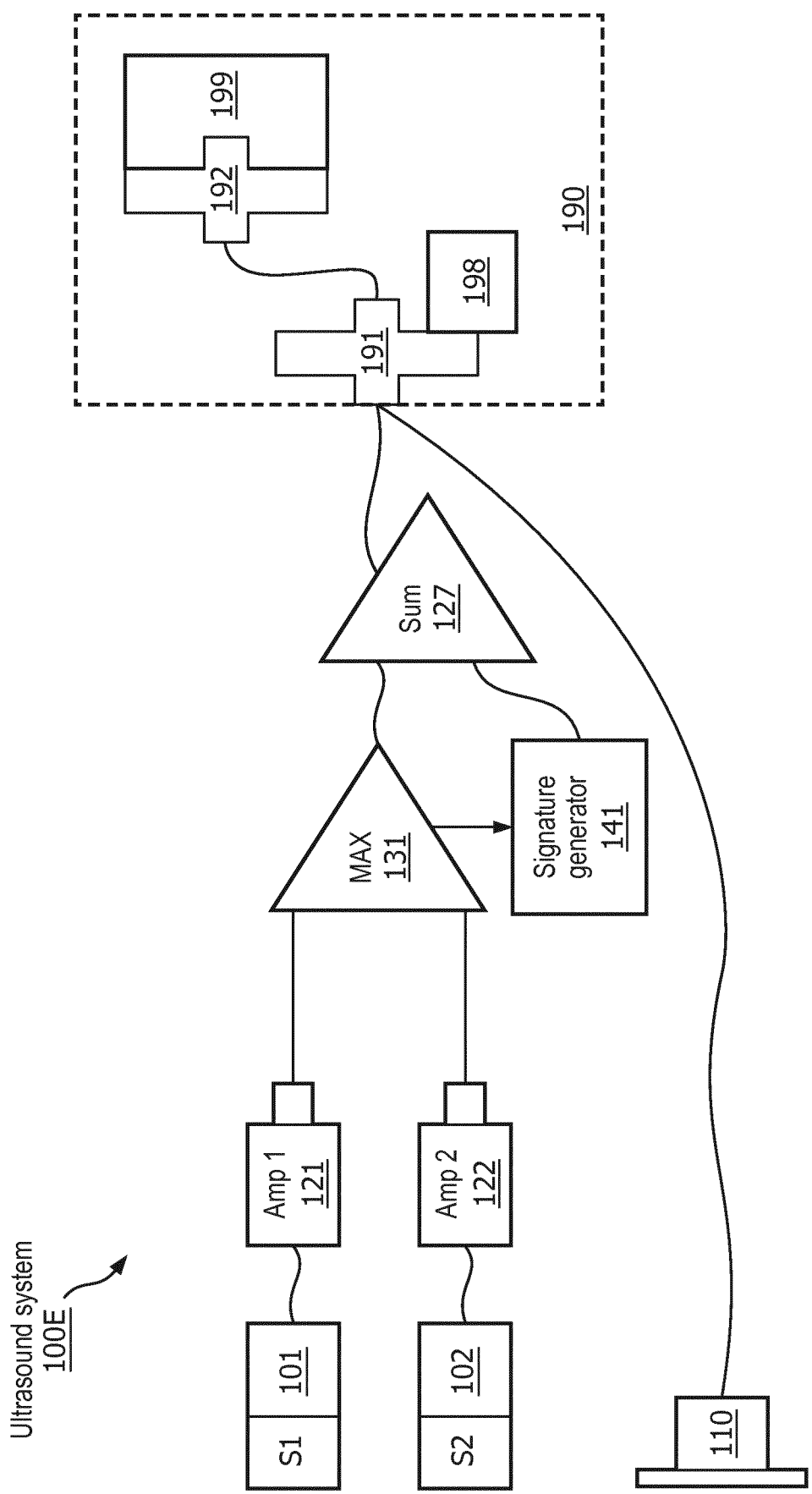
FIG. 5 illustrates another system for simultaneous sensor tracking in medical interventions, in accordance with another representative embodiment.

FIG. 5 illustrates another system for simultaneous sensor tracking in medical interventions, in accordance with another representative embodiment.

In FIG. 5, an ultrasound system 100E includes the first interventional medical device 101 with the first passive ultrasound sensor S1 disposed therein or thereon and the second interventional medical device 102 with the second passive ultrasound sensor S2 disposed therein or thereon. The first passive ultrasound sensor S1 is connected via the data connection to the first amplifier 121, and the second passive ultrasound sensor S2 is connected via the different data connection to a second amplifier 122. The output of the first amplifier 121 and the output of the second amplifier 122 are again provided to a maximum circuit 131 that identifies the peak magnitudes of each (i.e., both) of the first signal from the first passive ultrasound sensor S1 and the second signal from the second passive ultrasound sensor S2. However, in the embodiment of FIG. 5 a signature generator 141 is also provided, as well as the summer 127.

Specifically, in FIG. 5 the signature generator 141 and the summer 127 are used to determine what detected peak belongs to what device among the first passive ultrasound sensor S1 and the second passive ultrasound sensor S2. It is already known at all times which passive ultrasound sensor is currently producing the largest signal, and this information can be transmitted to the signature generator 141. The signature generator 141 creates a unique signal that depends on which passive ultrasound sensor has the maximum signal. This signal is then added to the maximum sensor signal, for later decoding by the downstream hardware.

In the embodiment of FIG. 5, the signature signals should not interfere with the peak detection. This can be addressed depending on how the first signal and the second signal are captured, such as by RF signal or envelope detection. For example, a device dependent DC offset can be added for an RF signal. For envelope detected data, high frequency signatures can be added that are outside the bandwidth of the sensor signal. Alternatively, interference can be avoided by adding a time delay to the signature signal so that the signature signal is placed in the unused data section, similar to the embodiment of FIGS. 2 and 3.

As described above, in the embodiment of FIG. 5, the process performed by a controller that includes the signature generator 141 and the summer 127 can include identifying that the first signal is from the first passive ultrasound sensor S1 and adding a unique electronic signature to the first signal. As a result, the single channel tracking system 190 (i.e., that determines the location of the first passive ultrasound sensor and the location of the second passive ultrasound sensor) can identify the first signal as being from the first passive ultrasound sensor S1. The controller can add a direct current (DC) offset to the first signal as the unique electronic signature. Alternatively, the controller can add a signature at a frequency outside of a bandwidth of the first signal as the unique electronic signature. As another alternative, the controller can insert a delay to the first signal as the unique electronic signature, so that the process executed by the controller includes inserting a delay to the first signal as the unique electronic signature.

Figure 6:
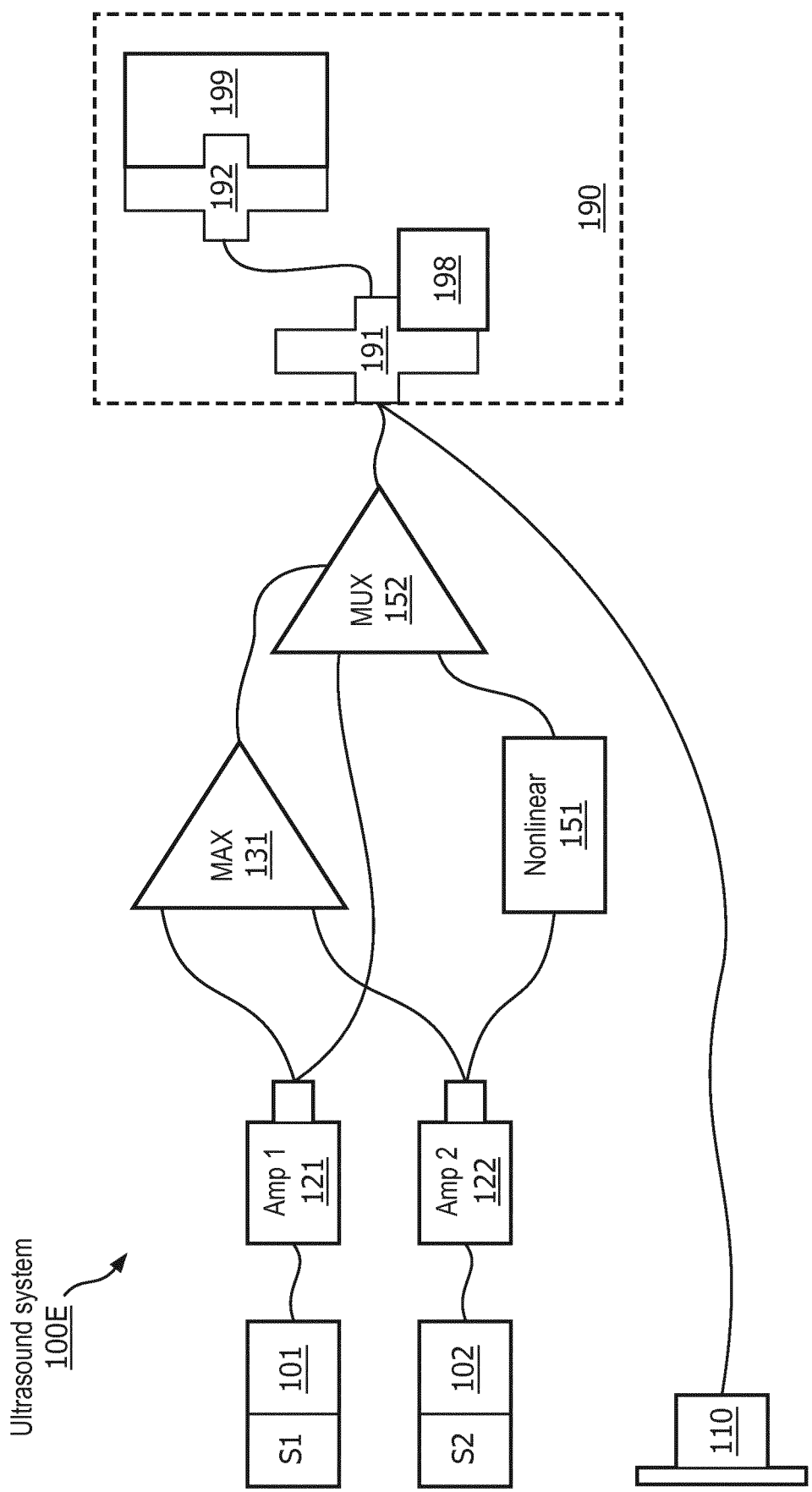
FIG. 6 illustrates another system for simultaneous sensor tracking in medical interventions, in accordance with another representative embodiment.

FIG. 6 illustrates another system for simultaneous sensor tracking in medical interventions, in accordance with another representative embodiment.

In FIG. 6, an ultrasound system 100E includes the first interventional medical device 101 with the first passive ultrasound sensor S1 disposed therein or thereon and the second interventional medical device 102 with the second passive ultrasound sensor S2 disposed therein or thereon. The first passive ultrasound sensor S1 is connected via the data connection to the first amplifier 121, and the second passive ultrasound sensor S2 is connected via the different data connection to a second amplifier 122. The output of the first amplifier 121 and the output of the second amplifier 122 are again provided to a maximum circuit 131 that identifies the peak magnitudes of each (i.e., both) of the first signal from the first passive ultrasound sensor S1 and the second signal from the second passive ultrasound sensor S2. However, in the embodiment of FIG. 6 a nonlinear circuit 151 and a multiplexer 152 are added to the circuit.

In the embodiment of FIG. 6, instead of adding a unique signature signal as in the embodiment of FIG. 5, the sensor signal itself is modified by sending it through a unique nonlinear transform via the nonlinear circuit 151. Here again, the maximum circuit 131 detects which of the first passive ultrasound sensor S1 and the second passive ultrasound sensor S2 is producing the maximum signal, but now this it is controlling the multiplexer 152. The signals from the first passive ultrasound sensor S1 and the second passive ultrasound sensor S2 each go through a unique/distinct transformation, and the multiplexer 152 selects the transformed sensor signal of the sensor with the original non-transformed magnitude that is the largest. The first signal and the second signal are both amplified, but only the signal from the maximum voltage sensor is selected by the multiplexer 152. MUX. If the passive ultrasound sensor S1 has the maximum voltage, its amplified signal is passed through unmodified. If the passive ultrasound sensor S2 has the maximum voltage, its amplified signal goes through a nonlinear transform by the nonlinear circuit 151 before being passed through. This nonlinear transform alters the spectral content of the amplified signal, allowing the downstream hardware to detect which passive ultrasound sensor it is from. This also allows the single channel tracking system to also perform the inverse transform on the appropriate amplified signal. Several examples of a usable nonlinear transforms for the embodiment of FIG. 6 include:

a frequency shift a logarithmic amplifier an absolute value (zero offset rectifier circuit)

In the embodiment of FIG. 6, a controller that includes the nonlinear circuit 151 and the multiplexer 152 modifies the first signal by processing the first signal through a unique nonlinear transform. The controller can determine that the largest peak of the first signal has a magnitude larger than a largest peak of the second signal and modify the first signal by processing the first signal through the unique nonlinear transform only based on determining that the largest peak of the first signal has the magnitude larger than the largest peak of the second signal. The second signal is not modified by a unique nonlinear transform when the largest peak of the second signal has the magnitude larger than the largest peak of the first signal.

Figure 7:
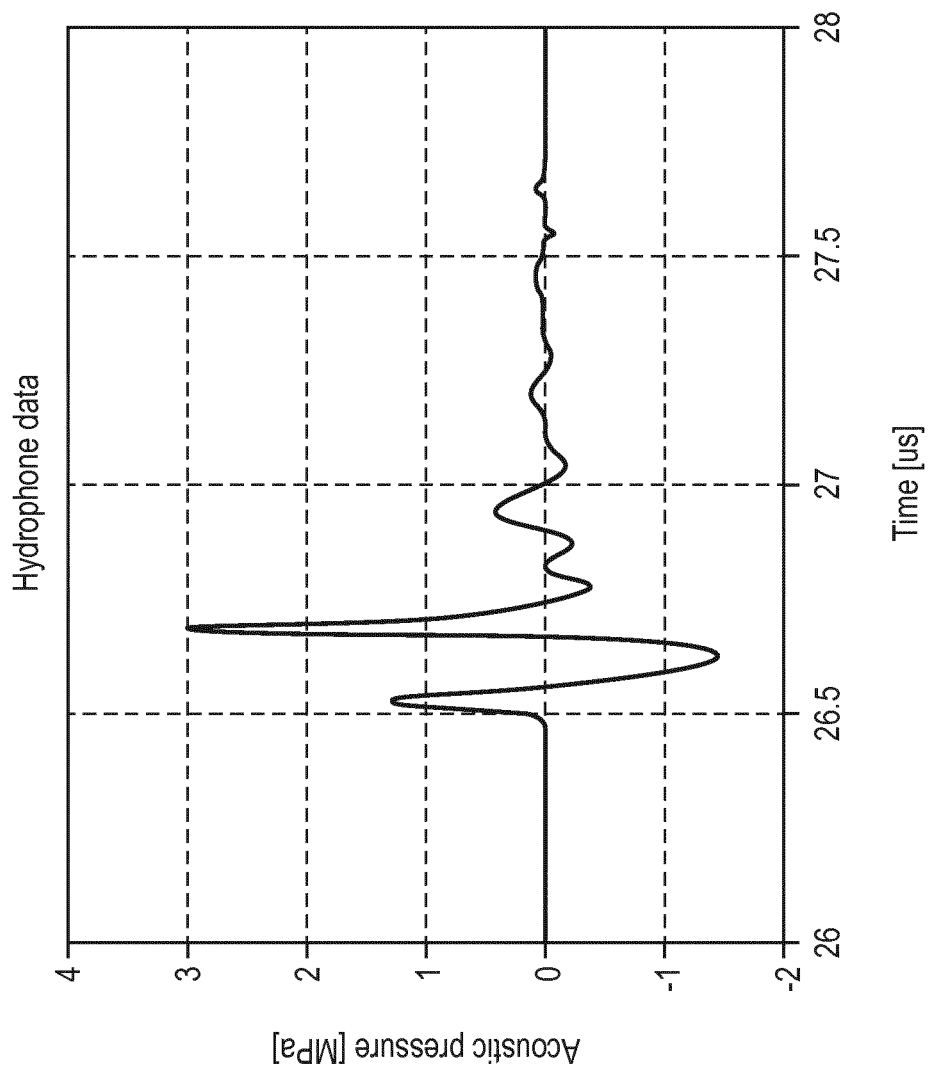
FIG. 7 illustrates pressure readings for a transmit pulse from an ultrasound probe, in accordance with another representative embodiment.

FIG. 7 illustrates pressure readings for a transmit pulse from an ultrasound probe, in accordance with another representative embodiment.

As context for the features shown in FIG. 7, the transmit pulse from an ultrasound probe 110 is often asymmetric. The peak negative pressure has regulatory limits that cannot be exceeded, but the peak positive pressure can be higher. In FIG. 7, the pressure pulse generated by an ultrasound probe 110 (e.g., a linear probe in a water tank as recorded with a hydrophone) is illustrated. The asymmetry in positive versus negative pressure can be exploited when two passive ultrasound sensors are involved by inverting the polarity of one of the passive ultrasound sensor.

Figure 8:
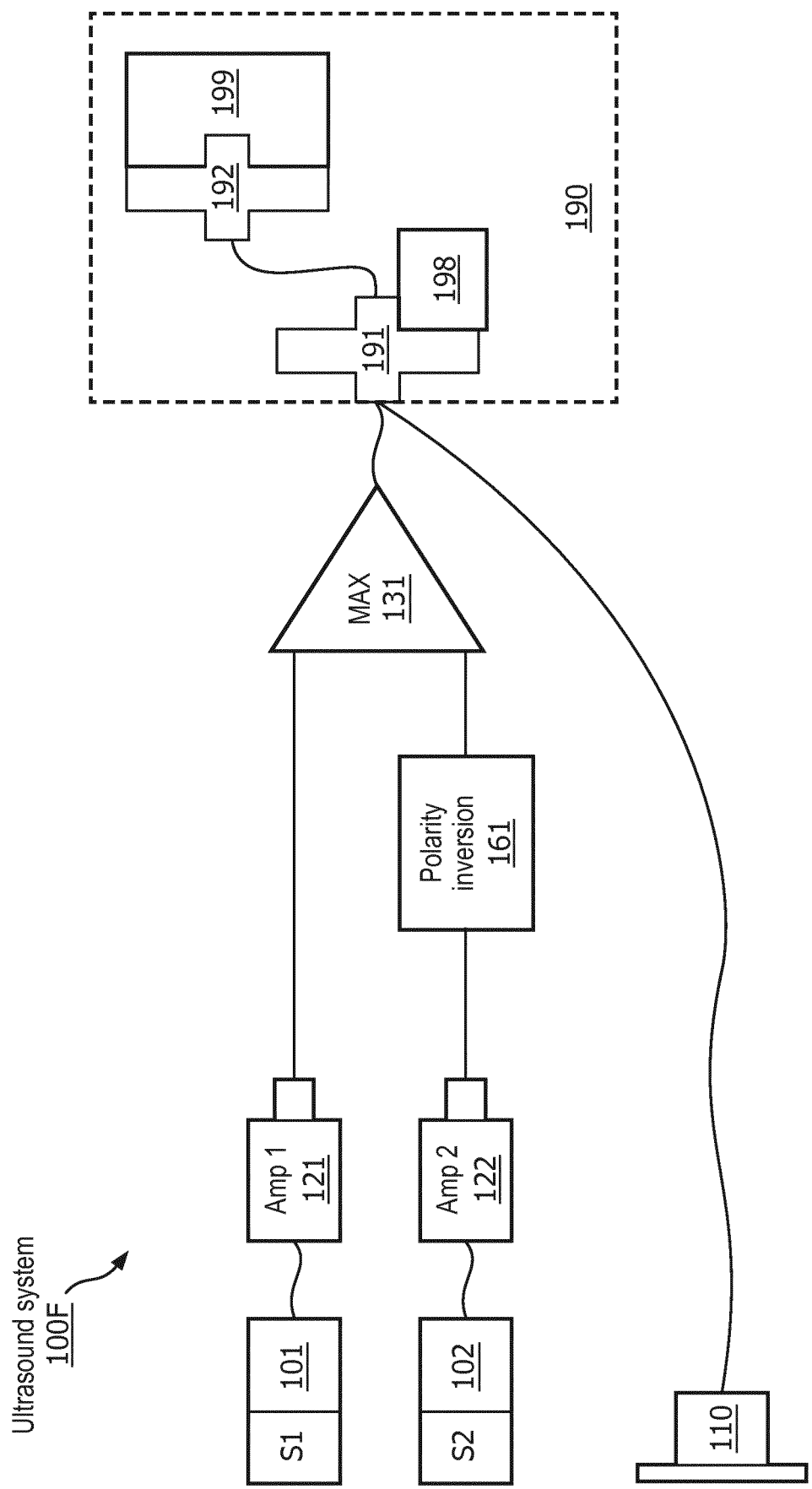
FIG. 8 illustrates another system for simultaneous sensor tracking in medical interventions, in accordance with the representative embodiment of FIG. 7.

FIG. 8 illustrates another system for simultaneous sensor tracking in medical interventions, in accordance with the representative embodiment of FIG. 7.

In FIG. 8, an ultrasound system 100F includes the first interventional medical device 101 with the first passive ultrasound sensor S1 disposed therein or thereon and the second interventional medical device 102 with the second passive ultrasound sensor S2 disposed therein or thereon. The first passive ultrasound sensor S1 is connected via the data connection to the first amplifier 121, and the second passive ultrasound sensor S2 is connected via the different data connection to a second amplifier 122. The output of the first amplifier 121 is provided direct to a maximum circuit 131, and the output of the second amplifier 122 is provided indirectly to the maximum circuit 131 via a polarity inversion circuit 161.

Similar to the embodiment of FIG. 5, in the embodiment of FIGS. 7 and 8, the sensor signal with the highest voltage is selected to be transmitted to the downstream hardware. Here, however, the signal for the second sensor has its polarity inverted. As a result, in the downstream hardware peak positive and peak negative voltage can be compared, and if peak positive voltage is higher the signal came from passive ultrasound sensor S1 and otherwise it is from passive ultrasound sensor S2.

As described above, in the embodiment of FIGS. 7 and 8, the controller that includes the polarity inversion circuit 161 and the maximum circuit 131 inverts polarity of one and only one of the first signal and the second signal. The single channel tracking system 190 identifies the first signal and the second signal based on which of the first signal and the second signal has a positive peak maximum.

Figure 9:
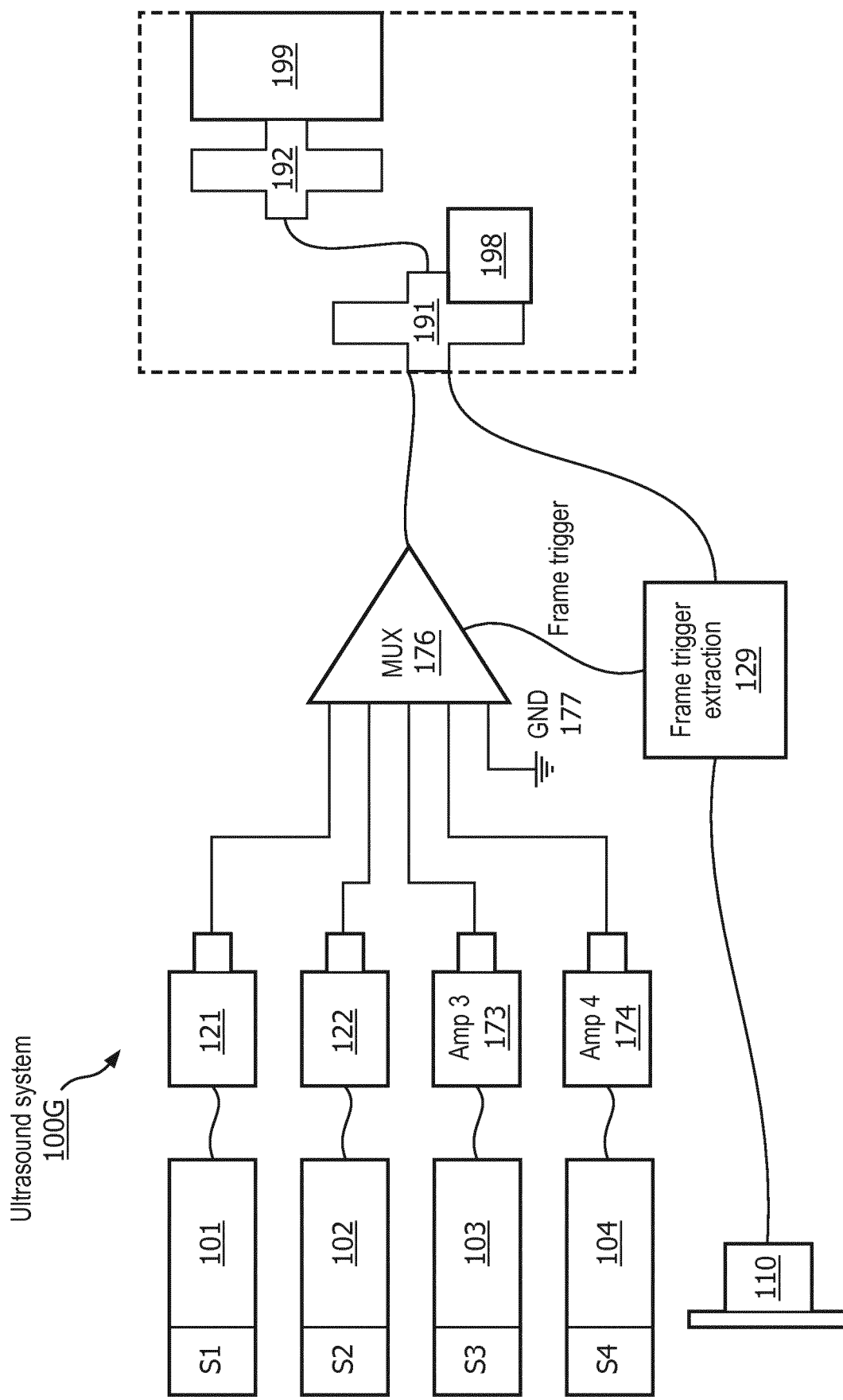
FIG. 9 illustrates another system for simultaneous sensor tracking in medical interventions, in accordance with another representative embodiment.

FIG. 9 illustrates another system for simultaneous sensor tracking in medical interventions, in accordance with another representative embodiment.

In FIG. 9, an ultrasound system 100G includes the first interventional medical device 101 with the first passive ultrasound sensor S1 disposed therein or thereon, the second interventional medical device 102 with the second passive ultrasound sensor S2 disposed therein or thereon, the third interventional medical device 103 with the third passive ultrasound sensor S3 disposed therein or thereon, and the fourth interventional medical device 104 with the fourth passive ultrasound sensor S4 disposed therein. The first passive ultrasound sensor S1 is connected via the data connection to the first amplifier 121, and the second passive ultrasound sensor S2 is connected via the different data connection to a second amplifier 122. The third passive ultrasound sensor S3 is connected via a data connection to a third amplifier 173, and the fourth passive ultrasound sensor S4 is connected via a data connection to a fourth amplifier 174. In the embodiment of FIG. 9, the output of the first amplifier 121, the output of the second amplifier 122, the output of the third amplifier 173 and the output of the fourth amplifier 174 are all provided to a multiplexer 176. Additionally, the frame trigger extraction circuit 129 is used to provide a frame trigger to the multiplexer 176.

In the embodiment of FIG. 9, the multiplexer 176 cycles through the passive ultrasound sensors and a tracking framerate is reduced to accommodate the multiple passive ultrasound sensors. The extracted frame trigger is used to advance the multiplexer 176 MUX from one passive ultrasound sensor to the next. One of the multiplexer 176 inputs may be a perfect 0 signal (Ground or GND), as this helps the downstream hardware in figuring out which passive ultrasound sensor is connected at any time. The embodiment of FIG. 9 reduces the tracking frame rate by a factor corresponding to one plus the number of devices (a factor of 5 for the four passive ultrasound sensors shown in FIG. 9). Accordingly, the process executed by a controller in FIG. 9 includes cycling one of the first signal from the first amplifier 121 and the second signal from the second amplifier 122 and the third signal from the third amplifier 173 and the fourth signal from the fourth amplifier 174 at a time using the multiplexer 176. The cycling may be performed based on an extracted frame trigger for each of the first signal, the second signal, the third signal and the fourth signal.

Alternatively, the frame trigger can be eliminated so that the multiplexer 176 is advanced at a fixed rate, and the cycling is therefore performed at a fixed rate. The switch times can be detected in the downstream hardware by detecting the locations of the regularly spaced step changes in signals caused by the switching. The framerate can additionally be improved, though slightly, by shortening the timespan of the multiplexer 176 for the GND input. The GND input may also be skipped entirely and a synchronization pulse can then be added in the unused data time window.

In the embodiment of FIG. 9, a controller that includes the frame trigger extraction circuit and the multiplexer 176 cycles the first signal and the second signal one at a time using the multiplexer 176 based on an extracted frame trigger for each of the first signal and the second signal. Alternatively, the controller cycles the first signal and the second signal one at a time using the multiplexer 176 at a fixed rate.

Figure 10:
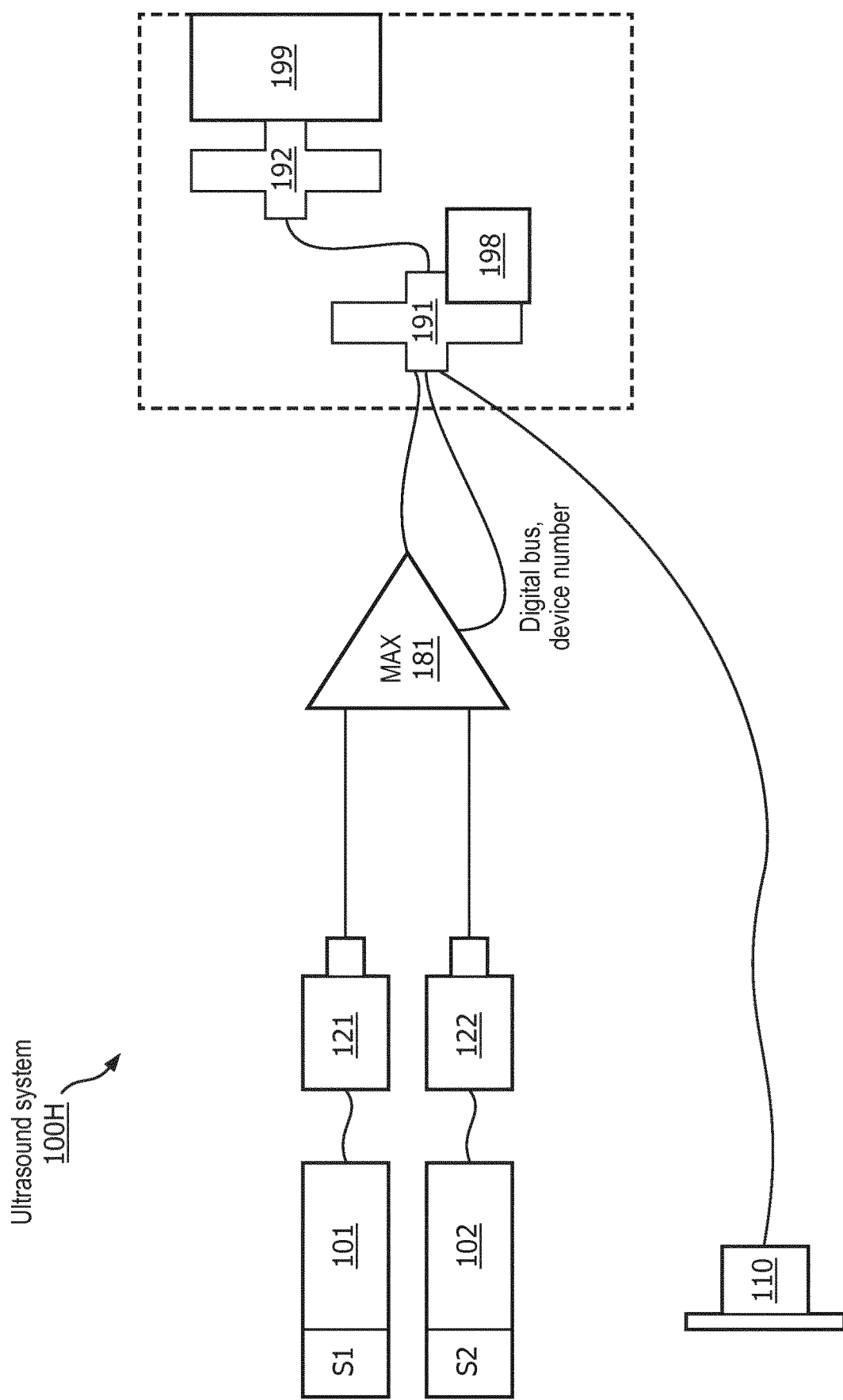
FIG. 10 illustrates another system for simultaneous sensor tracking in medical interventions, in accordance with another representative embodiment.

FIG. 10 illustrates another system for simultaneous sensor tracking in medical interventions, in accordance with another representative embodiment.

In FIG. 10, an ultrasound system 100G includes the first interventional medical device 101 with the first passive ultrasound sensor S1 disposed therein or thereon and the second interventional medical device 102 with the second passive ultrasound sensor S2 disposed therein or thereon. The first passive ultrasound sensor S1 is connected via the data connection to the first amplifier 121, and the second passive ultrasound sensor S2 is connected via the different data connection to a second amplifier 122. In the embodiment of FIG. 10, the output of the first amplifier 121 and the output of the second amplifier 122 are both provided to a maximum circuit 181.

In FIG. 10, the largest of the first signal and the second signal is detected and transferred to the downstream hardware. Additionally, the maximum circuit operates as a maximum signal detector and identifies which passive ultrasound sensor is generating the largest signal and creates a digital code such as a binary code indicating this passive ultrasound sensor. The binary code is then transmitted to the downstream hardware through a digital bus. The implementation of the embodiment in FIG. 10 may require a small modification to downstream hardware to accept a digital signal in addition to the sensor signal via the one and only one channel. However, the modification to the single channel tracking system 190 may be minor and can be accomplished using a digital input to a universal serial bus (USB) converter and putting it in an extra USB slot on the downstream hardware.

In the embodiment of FIG. 10, a binary code may be just one bit for only two passive ultrasound sensors. For example, the binary code may be 0 for the first passive ultrasound sensor S1 and 1 for the second passive ultrasound sensor S2. The digital bus may be just a single signal wire. Even with eight passive ultrasound sensors, only a 3-bit code is needed, and this code could be either transmitted in parallel over 3 wires or transmitted serially on a single signal line or over a standard serial bus such as RS232. Moreover, even an audio/microphone input may be used when using only existing inputs on downstream hardware, and frequency or amplitude can be modulated indicate the passive ultrasound sensor.

Simultaneous sensor tracking in medical interventions enables simultaneous tracking of multiple devices under ultrasound guidance for a range of clinical applications. For example, ablation devices can have independent prongs that are each localized for optimal placement of the ablation device. In treating atrial fibrillation, both an ablation catheter and a lasso catheter can be simultaneously tracked under ultrasound. The simultaneous tracking can be performed with even initial tracking systems with only a single sensor input, by retrofitting these initial systems with a signal combiner 120 as described herein. Such retrofitting can be cost effective and does not necessitate a visit from a technician or a modification to the tracking system that has only the single sensor input.

The controller described herein is implemented by different combinations of elements, components and devices of a circuit. However, a controller may also be implemented by a combination of a processor that executes instructions and a memory that stores the instructions, so long as the controller can interface with a single channel tracking system 190 and combine signals from multiple passive ultrasound sensors.

Although simultaneous sensor tracking in medical interventions has been described with reference to several exemplary embodiments, it is understood that the words that have been used are words of description and illustration, rather than words of limitation. Changes may be made within the purview of the appended claims, as presently stated and as amended, without departing from the scope and spirit of simultaneous sensor tracking in medical interventions in its aspects. Although simultaneous sensor tracking in medical interventions has been described with reference to particular means, materials and embodiments, simultaneous sensor tracking in medical interventions is not intended to be limited to the particulars disclosed; rather simultaneous sensor tracking in medical interventions extends to all functionally equivalent structures, methods, and uses such as are within the scope of the appended claims.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A controller for simultaneously tracking multiple sensors in a medical intervention, the controller comprising:
 a circuit operatively in communication with a tracking system over one and only one channel, the circuit configured to:
  receive, from a first passive ultrasound sensor of a first interventional medical device, a first signal with first sensor information indicative of a location of the first passive ultrasound sensor;
  receive, from a second passive ultrasound sensor of a second interventional medical device, a second signal with second sensor information indicative of a location of the second passive ultrasound sensor;
  combine the first signal and the second signal into a combined signal for transmission over the one and only one channel;
  perform a signal modification with respect to at least one of the first signal and the second signal that enables identification of the first signal and the second signal in the combined signal; and
  transmit the combined signal over the one and only one channel to a tracking system configured to track the first interventional medical device and the second interventional medical device, wherein the tracking device determines the location of the first passive ultrasound sensor and the location of the second passive ultrasound sensor from the combined signal based on the signal modification.

2. The controller of claim 1, wherein the circuit is further configured to:
 insert a delay with respect to either the first signal and the second signal in the combined signal.

3. The controller of claim 2,
 wherein the delay is removed from the combined signal by the tracking system.

4. The controller of claim 1, wherein the circuit is further configured to:
 isolate a largest peak of the first signal and a largest peak of the second signal;
 filter signal components with peaks smaller than the largest peak of the first signal and the largest peak of the second signal; and
 provide only signal components with the largest peak of the first signal and the largest peak of the second signal in the combined signal to the tracking system.

5. The controller of claim 4, wherein the circuit is further configured to:
 adjust amplifier gains of the first signal to generate a largest peak closer in magnitude to the largest peak of the second signal.

6. The controller of claim 1, wherein the circuit is further configured to:
 identify that the first signal is from the first passive ultrasound sensor by adding a unique electronic signature to the first signal in the combined signal.

7. The controller of claim 6, wherein the circuit is further configured to:
add a direct current offset to the first signal as the unique electronic signature.

8. The controller of claim 6, wherein the circuit is further configured to:
add a signature at a frequency outside of a bandwidth of the first signal as the unique electronic signature.

9. The controller of claim 6, wherein the circuit is further configured to:
insert a delay to the first signal as the unique electronic signature.

10. The controller of claim 1, wherein the circuit is further configured to:
modify the first signal by processing the first signal through a unique nonlinear transform.

11. The controller of claim 10, wherein the circuit is further configured to:
determine that a largest peak of the first signal has a magnitude larger than a largest peak of the second signal, and modify the first signal in the combined signal by processing the first signal through the unique nonlinear transform only based on determining that the largest peak of the first signal has the magnitude larger than the largest peak of the second signal,
wherein the second signal is not modified by a unique nonlinear transform when the largest peak of the second signal has the magnitude larger than the largest peak of the first signal.

12. The controller of claim 1, wherein the circuit is further configured to:
invert polarity of either the first signal or the second signal in the combined signal.

13. The controller of claim 12, wherein the tracking system identifies the first signal and the second signal based on which of the first signal and the second signal has a positive peak maximum.

14. The controller of claim 1, wherein the circuit is further configured to:
cycle only one of the first signal and the second signal at a time using a multiplexer based on an extracted frame trigger for each of the first signal and the second signal.

15. The controller of claim 1, wherein the circuit is further configured to:
cycle only one of the first signal and the second signal at a time using a multiplexer at a fixed rate.

16. The controller) of claim 4, wherein the circuit is further configured to:
determine which of the first signal and the second signal is larger; and
generate and send a digital code indicating which of the first signal and the second signal is larger.

17. A method for simultaneously tracking multiple sensors in a medical intervention, the method comprising:
receiving, from a first passive ultrasound sensor, a first signal with first sensor information indicative of a location of the first passive ultrasound sensor;
receiving, from a second passive ultrasound sensor, a second signal with second sensor information indicative of a location of the second passive ultrasound sensor;
combining the first signal and the second signal into a combined signal for transmission over one and only one channel;
performing a signal modification with respect to at least one of the first signal and the second signal that enables identification of the first signal and the second signal in the combined signal;
transmitting the combined signal over the one and only one channel to a tracking system configured to track the first interventional medical device and the second interventional medical device; and
determining, by the tracking system, the location of the first passive ultrasound sensor and the location of the second passive ultrasound sensor from the combined signal based on the signal modification.

18. A system for simultaneously tracking multiple sensors in a medical intervention, the system comprising:
an ultrasound probe configured to emit ultrasound beams in the medical intervention;
a first interventional medical device having a first passive ultrasound sensor configured to detect the ultrasound beams emitted from the ultrasound probe and generate, based on the ultrasound beams, a first signal with first sensor information indicative of a location of the first passive ultrasound sensor;
a second interventional medical device having a second passive ultrasound sensor configured to detect the ultrasound beams emitted from the ultrasound probe and generate, based on the ultrasound beams, a second signal with first sensor information indicative of a location of the second passive ultrasound sensor; and
a controller comprising a circuit configured to:
receive, from the first passive ultrasound sensor, the first signal with the first sensor information indicative of the location of the first passive ultrasound sensor,
receive, from the second passive ultrasound sensor, a second signal with the second sensor information indicative of the location of the second passive ultrasound sensor,
combine the first signal and the second signal into a combined signals for transmission over one and only one channel, and
perform a signal modification with respect to at least one of the first signal and the second signal that enables identification of the first signal and the second signal in the combined signal; and
a tracking device configured to track the first interventional medical device and the second interventional medical device, the tracking device having only the one and only one channel and configured to:
receive the combined signal over the one and only one channel from the controller, and
determine the location of the first passive ultrasound sensor and the location of the second passive ultrasound sensor from the combined signal based on the signal modification.

* * * * *